United States Patent
Kameyama et al.

(10) Patent No.: US 8,853,174 B2
(45) Date of Patent: Oct. 7, 2014

(54) AGENT FOR PREVENTING OR AMELIORATING SKIN AGING

(75) Inventors: Akiyo Kameyama, Haga-gun (JP); Tsutomu Fujimura, Haga-gun (JP)

(73) Assignee: Kao Corporation, Tokyo (JP)

( * ) Notice: Subject to any disclaimer, the term of this patent is extended or adjusted under 35 U.S.C. 154(b) by 372 days.

(21) Appl. No.: 12/867,958

(22) PCT Filed: Feb. 26, 2009

(86) PCT No.: PCT/JP2009/054097
§ 371 (c)(1),
(2), (4) Date: Aug. 17, 2010

(87) PCT Pub. No.: WO2009/107853
PCT Pub. Date: Sep. 3, 2009

(65) Prior Publication Data
US 2010/0331272 A1  Dec. 30, 2010

(30) Foreign Application Priority Data

Feb. 27, 2008 (JP) ................................ 2008-046490
Feb. 16, 2009 (JP) ................................ 2009-032434

(51) Int. Cl.
*A01N 43/04* (2006.01)
*A61K 31/70* (2006.01)
*A61Q 19/08* (2006.01)
*A61K 8/63* (2006.01)
*A61K 8/97* (2006.01)
*C07H 15/256* (2006.01)

(52) U.S. Cl.
CPC .............. *C07H 15/256* (2013.01); *A61Q 19/08* (2013.01); *A61K 8/63* (2013.01); *A61K 8/97* (2013.01)
USPC ........................................................ 514/33

(58) Field of Classification Search
CPC ......... A61K 8/97; A61K 8/63; C07H 15/526; A61Q 19/08
USPC ........................................................ 514/33
See application file for complete search history.

(56) References Cited

U.S. PATENT DOCUMENTS

| | | | |
|---|---|---|---|
| 4,826,828 A | 5/1989 | Wilmott et al. | |
| 5,296,500 A | 3/1994 | Hillebrand | |

FOREIGN PATENT DOCUMENTS

| | | |
|---|---|---|
| EP | 0358880 A2 | 3/1990 |
| EP | 0379367 A2 | 7/1990 |
| JP | 62-185005 | 8/1987 |
| JP | 62-502546 | 10/1987 |
| JP | 02-072157 A | 3/1990 |
| JP | 02-288822 A | 11/1990 |
| JP | 06-510542 A | 11/1994 |
| JP | 07-041419 A | 2/1995 |
| JP | 10-17591 A | 1/1998 |
| JP | 2004-339113 A | 12/2004 |
| JP | 2005-008571 A | 1/2005 |
| JP | 2005 008571 A | 1/2005 |

OTHER PUBLICATIONS

Definition of "prevention" from the Institute for International Medical Education [online], [Retrieved on Mar. 24, 2011]. Retrieved from the Internet <http://www.iime.org/glossary.htm>. Published Feb. 2002, p. 1, 2, 26, 27 and 39.*

"Causes of Aging Skin" from AgingSkinNet [online], [Retrieved on Aug. 28, 2012]. Retrieved from the iinternet <http://www.skincarephysicians.com/agingskinnet/basicfacts.html>.*

Snodgrass, W.R. (2001) Herbal Products: Risks and Benefits of Use in Children. Current Therapeutic Research, vol. 62, No. 10, p. 724-735.*

International Search Report for PCT/JP2009/054097, mailed Sep. 29, 2009 from the European Patent Office, Rijswijk, the Netherlands.

International Preliminary report on Patentability issued Aug. 31, 2010, including the Written Opinion of the International Searching Authority for PCT/JP2009/054097, The International Bureau of WIPO, Geneva, Switzerland.

(Continued)

*Primary Examiner* — Scarlett Goon
(74) *Attorney, Agent, or Firm* — Sterne, Kessler, Goldstein & Fox P.L.L.C.

(57) ABSTRACT

An agent for preventing or ameliorating skin aging, which exhibits a more excellent effect on the suppression of formation, or the amelioration, of wrinkles on the skin or sagging skin. An agent for preventing or ameliorating skin aging, containing triterpenoid saponins represented by the following formula (1) as an active ingredient, wherein at least one of $R^1$ and $R^2$ is a tigloyl group and the other represents a tigloyl group or an angeloyl group; $R^3$ represents a methyl group or a hydroxymethyl group; and $R^4$ represents Glc, Xyl or Gal.

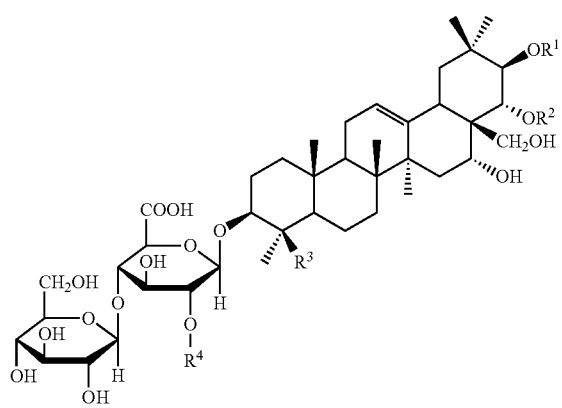

11 Claims, 4 Drawing Sheets

(56) References Cited

OTHER PUBLICATIONS

Matsuda, H. et al., "Antiinflammatory effects of escins Ia, Ib, IIa, and IIb from horse chestnut, the seeds of *Aesculus hippocastanum* L," Bioorganic & Medicinal Chemistry Letters 7(13): 1611-1616 (Jul. 1997), Pergamon, Elsevier Science.

Matsuda, H. et al., "Effects of escins Ia, Ib, IIa, and IIb from horse chestnut, the seeds of *Aesculus hippocastanum* L, on acute inflammation in animals," Biological and Pharmaceutical Bulletin (of Japan) 20 (10): 1092-1095 (Oct. 1997), Pharmaceutical Society of Japan, Tokyo, JP.

Sati, O. et al., "A new molluscicidal triterpenic glycoside from *Aesculus indica*," Int. J. Crude Drug Res. 25: 158-160 (1987), Swets & Zeitlinger B.V.

Yoshikawa, M. et al., "Bioactive saponins and glycosides. XII. Horse chestnut. (2): Structures of escins IIIb, IV, V, and VI and isoescins Ia, Ib, and V, acylated polyhydroxyoleanene triterpene oligoglycosides, from the seeds of horse chestnut tree (*Aesculus hippocastanum* L., Hippocastanaceae).," Chem. Pharm Bull (Tokyo) 46:1764-1769 (Nov. 1998), Pharmaceutical Society of Japan.

Zhang, Z. et al., "New saponins from the seeds of *Aesculus chinensis*," Chem Pharm Bull (Tokyo) 47(11): 1515-1520 (Nov. 1999), Pharmaceutical Society of Japan, Tokyo, JP.

Formulation MA3/290, Sufoof-e-Sandali, India Traditional Knowledge Database Library (TKDL) extract, English translation and terminology conversion of Mohammad Kabiruddin, Bayaaz-e-Kabir, vol. II (Compiled), Daftar-al-Maseeh, Karol Bagh, New Delhi, 1938, p. 88.

Formulation RS/4019, Candanagunaāh, India Traditional Knowledge Database Library (TKDL) extract, English translation and terminology conversion of Braht Nighantu Ratnākara (Saligramanighantubhusanam)—compiled by Gaṅgāvisnu Śrikrsna Dāsa, Translated by Sri Dattarama Srikrsnalala Mathura; vol. 4 (Part III), 1997 edition, Khemaraja Srikrsnadas Prakasana, Mumbai-4, p. 12.

Formulation RS/4379, Kanda GuducīGunaāh, India Traditional Knowledge Database Library (TKDL) extract, English translation and terminology conversiion of Mahendra Bhaugika; Dhanvantarinighantauh—Edited by P.V. Sharma; translated by Guru Prasad Sharma; Chaukhambha Orientalia, Varanasi, $3^{rd}$ edition, 2002, p. 17.

Formulation MH3/116A, Safoof-e-Asgand, India Traditional Knowledge Database Library (TKDL) extract, English translation and terminology conversion of Mohammad Azam Khan; Muheet-e-Azam, vol. I ($19^{th}$ century AD), Matba Nizami, Kanpur, 1896, p. 156.

Formulation NA2/149G, Ubtan-e-Aqaqia, India Traditional Knowledge Database Library (TKDL) extract, English translation and terminology conversion of Mohammad Najmul Ghani Khan; Khazaain-al-Advia, vol. I ($20^{th}$ Century), Nadeem Yunus Printer / Sheikh Mohd Basheer & Sons, Lahor, 1911, p. 551.

Formulation AK/4041B, Catvārirasāyanam (2), India Traditional Knowledge Database Library (TKDL) extract, English translation and terminology conversion of Govinda Dāsa; Bhaisajya Ratnāvalī—edited by Rajeshvaradutta Shastri, Translated by Ambikaduttashastri : Chaukhamba Sanskrit Sansthan, Varanasi, $14^{th}$ edition, 2001, p. 766.

Formulation AN2/729U, Raughan Zaitoon Muhassin-e-laun, India Traditional Knowledge Database Library (TKDL) extract, English translation and terminology conversion of Mohammad Najmul Ghani Khan; Khazaain-al-Advia, vol. II ($20^{th}$ Century), Nadeem Yunus Printer / Sheikh Mohd Basheer & Sons, Lahor, 1911, p. 725.

Formulation AN2/786A, Obtran Sarson Barae Kalaf, India Traditional Knowledge Database Library (TKDL) extract, English translation and terminology conversion of Mohammad Najmul Ghani Khan; Khazaain-al-Advia, vol. II ($20^{th}$ Century), Nadeem Yunus Printer / Sheikh Mohd Basheer & Sons, Lahor, 1911, p. 781.

Formulation BP/123, Gandhakayogah (03), India Traditional Knowledge Database Library (TKDL) extract, English translation and terminology conversion of Bhārata Bhaisajya Ratnākara—Compiled by Nagīnadāsa Chaganalāla Śāha, Translated by Gopinath Gupta—vol. II:B, Jain pulishers, New Delhi, $2^{nd}$ edition, reprint, Aug. 1999, p. 22.

Formulation SS02/479, Vathumai Nasiyam, India Traitional Knowledge Database Library (TKDL) extract, English translation and terminology conversion of Therayar; Therayar Venba.CCRAS Publications, Chennai, p. 262, (1975).

\* cited by examiner

AGENT FOR PREVENTING OR AMELIORATING SKIN AGING

FIELD OF THE INVENTION

The present invention relates to an agent for preventing or ameliorating skin aging, which has an effect of suppressing or ameliorating the formation of wrinkles or sagging skin.

BACKGROUND OF THE INVENTION

To retain healthy and beautiful skin is an issue of very much concern, in particular for women. However, the condition of the skin is constantly under the influence of factors such as humidity, ultraviolet rays, increasing age, diseases, stress and dietary habits, and as a result, there occur various skin troubles, such as deterioration of general functions of the skin and aging of the skin.

Among others, wrinkles or sagging skin develop as a consequence of aging of the skin due to increasing age, photo-aging due to the exposure to sunlight, etc. That is, the cells producing dermal fibers become smaller in both size and number, and particularly a large quantity of collagen fibers are lost, concomitantly with exposure to sunlight or an increase in the age. Thus, degeneration of the dermis, reduction of the subcutaneous adipose tissue, and the like lead to the aging of the skin, and this aging mainly causes wrinkles, laxity of the skin and loss of skin elasticity.

There have been hitherto proposed compositions or methods for suppressing or ameliorating the aging process including such wrinkles, sagging skin and the like (Patent Document 1, Patent Document 2, Patent Document 3, Patent Document 4, Patent Document 5 and Patent Document 6), but their effects were not necessarily sufficiently satisfactory.

Therefore, the applicant of the present invention found that the extract of horse chestnut (*Aesculus hippocastanum*) has an excellent action of ameliorating wrinkles, and filed a patent application before (Patent Document 7). However, it was not completely clear of what component present in horse chestnut attains the manifestation of the aforementioned action.

Patent Document 1 JP-A-62-185005
Patent Document 2 JP-A-62-502546
Patent Document 3 JP-A-02-72157
Patent Document 4 JP-A-02-288822
Patent Document 5 JP-A-07-41419
Patent Document 6 JP-A-06-510542
Patent Document 7 JP-A-2005-8571

SUMMARY OF THE INVENTION

The present invention is directed to an agent for preventing or ameliorating skin aging, the agent including triterpenoid saponins represented by the following formula (1) as an active ingredient:

wherein at least one of $R^1$ and $R^2$ is a tigloyl group and the other represents a tigloyl group or an angeloyl group; $R^3$ represents a methyl group or a hydroxymethyl group; and $R^4$ represents Glc, Xyl or Gal.

The present invention is also directed to an external preparation for skin, comprising 0.00001 to 2% by mass of triterpenoid saponins represented by the above formula (1).

The present invention is also directed to use of triterpenoid saponins represented by the above formula (1), for the production of an agent for preventing or ameliorating skin aging.

The present invention is also directed to a method for preventing or ameliorating skin aging, including applying triterpenoid saponins represented by the above formula (1) to a human body.

Furthermore, the present invention is also directed to triterpenoid saponins represented by the following formula (1a):

wherein at least one of $R^1$ and $R^2$ is a tigloyl group and the other represents a tigloyl group or an angeloyl group; $R^3$ represents a methyl group or a hydroxymethyl group; and $R^4$ represents Glc, Xyl or Gal, with the proviso that the case wherein $R^1$ is a tigloyl group; $R^2$ is a tigloyl group or an angeloyl group; $R^3$ is a hydroxymethyl group; and $R^4$ is Glc is excluded.

DETAILED DESCRIPTION OF THE INVENTION

The present invention relates to the provision of cosmetic products, pharmaceutical products and the like, which exhibit more excellent effects in suppression of formation, or amelioration, of skin wrinkles or sagging skin.

The inventors of the present invention conducted an investigation on the components contained in horse chestnut, and as a result, they unexpectedly found that triterpenoid saponins represented by the formula (1) shown above, which is a minor component contained in the seeds of horse chestnut, have an action of significantly enhancing the contraction force generated by skin fibroblasts, and is useful for the prevention or amelioration of wrinkles or sagging skin. The triterpenoid saponins are novel compounds which are represented by the formula (1a), except for some derivatives thereof.

The agent for preventing or ameliorating skin aging and the external preparation for skin of the present invention exhibit an effect of suppressing the formation of wrinkles or sagging skin, or of ameliorating wrinkles or sagging skin. The agents and the external preparation of the present invention are useful as cosmetic products, pharmaceutical products and the like which suppress formation of wrinkles or sagging skin, make the appearance of wrinkles or sagging skin inconspicuous, or can remove wrinkles or sagging skin.

Among the triterpenoid saponins represented by the formula (1) of the present invention, a compound in which $R^1$ is a tigloyl group, $R^2$ is a tigloyl group or an angeloyl group, $R^3$ is a hydroxymethyl group and $R^4$ is Glc, is a known compound, and other compounds (formula (1a)) are novel compounds.

In the formula (1) and (1a), $R^3$ is preferably a hydroxymethyl group, wherein $R^1$ is preferably a tigloyl group, wherein $R^2$ is preferably a tigloyl group, in view of the effect of ameliorating wrinkles or sagging skin, i.e. in view of contraction force generated by skin fibroblasts.

Furthermore, $R^4$ is preferably Glc or Xyl, and more preferably Glc.

In the formulas, Glc represents a glucose residue, Gal a galactose residue, and Xyl a xylose residue.

Representative examples of the triterpenoid saponins of the present invention are shown below.

TABLE 1

| | $R^1$ | $R^2$ | $R^3$ | $R^4$ |
|---|---|---|---|---|
| Compound 1 | Tig | Tig | CH$_2$OH | Glc |
| Compound 2 | Tig | Ang | CH$_2$OH | Glc |
| Compound 3 | Ang | Tig | CH$_2$OH | Glc |
| Compound 4 | Tig | Tig | CH$_2$OH | Xyl |
| Compound 5 | Ang | Tig | CH$_2$OH | Xyl |
| Compound 6 | Tig | Tig | CH$_3$ | Gal |

Tig: Tigloyl group,
Ang: Angeloyl group

It has been reported that the seeds of horse chestnut contain escin derivatives such as Escin Ia ($R^1$: tigloyl group, $R^2$: acetyl group, $R^3$: hydroxymethyl group, $R^4$: Glc) and Escin Ib ($R^1$: angeloyl group, $R^2$: acetyl group, $R^3$: hydroxymethyl group, $R^4$: Glc), which have an acetyl group as $R^2$, as a main ingredient (Chem. Pharm. Bull. 46(11), 1764-1769 (1998)). As shown in the Test Examples described below, however, the escin derivatives showed no effect of enhancing the contraction force as observed in the compound of the present invention.

The triterpenoid saponins (1) of the present invention, including the compound (1a), can be obtained by separating and purifying an extract which is prepared by solvent extraction from seeds of a plant belonging to the genus *Aesculus*, such as horse chestnut (*Aesculus hippocastanum L.*), Tochino-ki (*Aesculus turbinata*) or Chinese horse chestnut (*Aesculus chinensis*), using appropriate means for separation and purification such as column chromatography, ion exchange chromatography and high performance liquid chromatography. Hereinbelow, an example of isolation of the compound will be described.

1) An ethanol-water mixed solution is added to a ground product of seeds of horse chestnut, and extraction is carried out while the mixture is stirred under heating, to thereby obtain an extract of horse chestnut.

2) The extract obtained in 1) is passed through a column packed with Diaion HP20, to adsorb saponin components. The adsorbed saponins are eluted with 99.5 vol % ethanol, to obtain a mixture A.

3) The mixture A obtained in 2) is dissolved in 70 vol % methanol, hexane is added to the solution, and the mixture is mixed by shaking in a separatory funnel to separate the mixture into layers. The 70 vol % methanol layer is concentrated under reduced pressure and freeze-dried, to obtain a mixture B.

4) The mixture B obtained in 3) is subjected to flash column chromatography with a column packed with ODS, and to sequential elution with a mixed solution of methanol:water (volume ratio 50:50→90:10→100:0), to thereby obtain a mixture C.

5) The mixture C obtained in 4) is subjected to flash column chromatography with a column packed with silica gel, and to sequential elution with a mixed solution of chloroform:methanol:water (8:2:1→7:3:0.5→6:4:1→ methanol only), to thereby obtain a mixture D.

6) The mixture D obtained in 5) is subjected to medium pressure chromatography equipped with an ODS column, and to sequential elution with 1% acetic acid-70 volt methanol and 1% acetic acid-methanol, to thereby obtain a mixture E which mainly contains diacylated triterpenoid saponins.

7) The mixture E obtained in 6) is subjected to high performance liquid chromatography equipped with an ODS column, and is fractionated with 45 vol % acetonitrile added with 0.005% trifluoroacetic acid, to thereby obtain saponins a to g shown in the following Table 1 and Table 2.

8) The saponin g obtained in 7) is subjected to recycling preparative high performance liquid chromatography to obtain g-1 and g-2.

Furthermore, when such extraction and fractionation are carried out, the triterpenoid saponins (1) may be obtained alone or as a mixture of several species, but concerning the agent for preventing or ameliorating skin aging and the external preparation for skin of the present invention, any of these can be used.

The triterpenoid saponins represented by the formula (1) of the present invention have an action of enhancing the contraction force generated by skin fibroblasts, as will be described in the following Examples. The contraction force generated by skin fibroblasts is attributed to formation of stress fibers which accompanies actin polymerization, and a substance which enhances the contraction force generated by skin fibroblasts is suggested to be effective for preventing or ameliorating aging of skin tissue, namely, sagging of the skin, reduced resilience, wrinkles, and the like (J. Cosmet. Sci., 57, 369-376, 2006).

Therefore, the triterpenoid saponins of the present invention can be used as an agent for preventing or ameliorating skin aging or an external preparation for skin, which exhibits actions such as prevention or amelioration of wrinkles and amelioration of skin elasticity, and the compound can be used for the production of an agent for preventing or ameliorating skin aging or an external preparation for skin. The agent for preventing or ameliorating skin aging or the external preparation for skin can be used as cosmetic products, pharmaceutical products, quasi-drugs, and the like.

Furthermore, the cosmetic products or quasi-drugs containing the triterpenoid saponins of the present invention contain the triterpenoid saponins of the present invention, and can indicate the purpose of preventing or ameliorating skin aging, preventing or ameliorating wrinkles, and preventing or ameliorating the reduction of elasticity or resilience of the skin.

In the case of using the agent for preventing or ameliorating skin aging of the present invention as a pharmaceutical product, the route of administration may be exemplified by, for example, oral administration by means of tablets, capsules, granules, powders, syrups and the like, or parenteral administration by means of injections, suppositories, inhalants, transdermally absorbable preparations, external preparations and the like. An external preparation for skin which is applied to the skin is preferred. When pharmaceutical preparations of such various dosage forms are to be prepared, the triterpenoid saponins represented by the formula (1) of the present invention can be used alone, or in appropriate combination with other pharmaceutically acceptable excipients such as vehicles, binding agents, bulking agents, disintegrants, surfactants, lubricants, dispersants, buffering agents, preservatives, flavoring agents, fragrances, film-forming agents, carriers, diluents and the like.

In the case of using the agent for preventing or ameliorating skin aging or the external preparation for skin of the present invention as a quasi-drug or a cosmetic material, the agent can be prepared into a cleanser, a makeup cosmetic material or the like, and the agent can be provided in various preparation forms such as lotion, emulsion, cosmetic toner, gel, cream, gel, paste, cataplasm, plaster, stick, sheet, ointment, powder and granule depending on their usage.

The quasi-drugs or cosmetic materials of such various preparation forms can be prepared by using the triterpenoid saponins represented by the formula (1) of the present invention alone, or by appropriately combining the triterpenoid compound with a component which can be incorporated in quasi-drug, skin cosmetic material and cleansing material, such as oil components such as plant oils and animal oils, drugs (for example, allantoin, vitamin E derivatives, glycyrrhizin, anti-inflammatory agents such as ascorbic acid derivatives, antioxidants such as α-tocopherol and ascorbic acid, ultraviolet absorbents, pain and inflammation alleviating agents, sterilizing disinfectants, astringents, skin softeners, hormones, or vitamins), moisturizers, alcohols, chelating agents, pH adjusting agents, antiseptics, thickening agents, colorants, fragrances and the like.

The amount of the triterpenoid saponins represented by the formula (1) incorporated into the agent for preventing or ameliorating skin aging and the external preparation for skin, is preferably 0.00001 to 2% by mass, more preferably 0.0001 to 0.5% by mass, and even more preferably 0.001 to 0.1% by mass. Also, the amount of administration of the agent for preventing or ameliorating skin aging is, in terms of the triterpenoid compound, preferably 0.001 to 200 mg, more preferably 0.01 to 50 mg, and even more preferably 0.1 to 10 mg, per day.

EXAMPLES

Production Example 1

(1) 500 g of seeds of horse chestnut (*Aesculus hippocastanum* L.) were ground and then pneumatic-separated to remove peeled hulls. To 400 g of the ground product of seeds mainly containing the endosperm, 4 L of a mixed solution of ethanol and water (volume ratio 50:50) was added, and the mixture was extracted while being stirred for 6 hours under heating at 50° C. The heating and stirring was stopped, and the extract was left to cool to room temperature, and then filtered. A mixed solution of ethanol and water (4 L, volume ratio 50:50) was added again to the residue, and extraction was performed in the same manner. The extract was filtered, and the filtrate was combined with the previous filtrate, to obtain a horse chestnut extract. The extracted solid content in the extract was about 90 g.

(2) The extract obtained in (1) was passed through a column packed with Diaion HP20, to thereby adsorb saponin components including the target component. The column was washed with 50 vol % ethanol, and the adsorbed saponins were eluted with 99.5 vol % ethanol, to obtain 7.0 g of a mixture A.

(3) 7.0 g of the mixture A obtained in (2) was dissolved in 70 vol % methanol, and hexane was added thereto. The mixture was mixed by shaking in a separatory funnel, and then left to stand still at room temperature, to separate the mixture into layers. The 70 vol % methanol layer was concentrated under reduced pressure and freeze-dried to obtain 5.2 g of a mixture B.

(4) 5.2 g of the mixture B obtained in (3) was subjected to flash column chromatography with a column packed with ODS, and sequential elution was carried out with a mixed solution of methanol:water (volume ratio 50:50→90:10→100:0), to thereby obtain 3.8 g of a mixture C which contained the target component. Here, in the mixture C, the components other than the target component were mostly escin derivatives.

(5) 3.8 g of the mixture C obtained in (4) was subjected to flash column chromatography with a column packed with silica gel, and sequential elution was carried out with a mixed solution of chloroform:methanol:water (8:2:1→7:3:0.5→6:4:1→ methanol only), to thereby obtain 2.8 g of a mixture D containing the target component.

(6) 2.8 g of the mixture D obtained in (5) was subjected to medium pressure chromatography equipped with an ODS column, and was sequentially eluted with 1% acetic acid-70 vol % methanol and 1% acetic acid-methanol, to thereby obtain 442.4 mg of a mixture E which mainly contained diacylated triterpenoid saponins.

(7) From the mixture E obtained in (6), 40.0 mg was subjected to high performance liquid chromatography equipped with an ODS column, and was fractionated with 45 vol % acetonitrile added with 0.005% trifluoroacetic acid, to thereby obtain 2.1 mg of saponin a (compound 4), 6.8 mg of saponin b (compound 1), 2.7 mg of saponin c (compound 2), 0.9 mg of saponin d (compound 5), 3.0 mg of saponin e (compound 3), 1.1 mg of saponin f, and 4.3 mg of saponin g. The saponins a to f were analyzed, and were confirmed to be single compounds.

(8) The saponin g obtained in 7) was fractionated by recycling preparative high performance liquid chromatography to obtain 1.5 mg of saponin g-1 and 1.3 mg of saponin g-2 (compound 6).

Furthermore, among the extracts of horse chestnut, most of the activity of enhancing the contraction force generated by cells described in the following Examples, was found in the mixture E.

$^{13}$C-NMR spectral data of the obtained compounds are presented in Tables 2 and 3.

TABLE 2

| | a Compound 4 | b Compound 1 | c Compound 2 | d Compound 5 | e Compound 3 | f — | g-1 — | g-2 Compound 6 |
|---|---|---|---|---|---|---|---|---|
| | $^{13}$C-NMR Data for the Aglycone Moieties (125 MHz in Pyridine-d5) | | | | | | | |
| 1 | 38.8 | 38.5 | 38.5 | 39.8 | 38.5 | 38.8 | 38.5 | 38.8 |
| 2 | 26.7 | 26.6 | 26.6 | 26.6 | 26.6 | 26.6 | 26.5 | 26.6 |
| 3 | 90.7 | 91.1 | 91.1 | 90.7 | 91.1 | 90.6 | 91.1 | 89.3 |
| 4 | 44.3 | 43.7 | 43.7 | 43.7 | 43.7 | 44.3 | 43.7 | 39.6 |
| 5 | 56.3 | 56.1 | 56.1 | 56.3 | 56.1 | 56.3 | 56.1 | 55.7 |
| 6 | 18.7 | 18.5 | 18.5 | 18.7 | 18.5 | 18.7 | 18.5 | 18.4 |
| 7 | 33.3 | 33.2 | 33.2 | 33.3 | 33.2 | 33.3 | 33.2 | 33.1 |
| 8 | 40.0 | 39.9 | 40.0 | 40.0 | 40.0 | 40.0 | 40.0 | 40.1 |
| 9 | 46.8 | 46.7 | 46.7 | 46.7 | 46.7 | 46.8 | 46.7 | 46.9 |
| 10 | 36.5 | 36.5 | 36.6 | 36.5 | 36.4 | 36.5 | 36.4 | 36.8 |
| 11 | 24.1 | 24.1 | 24.1 | 24.0 | 24.1 | 24.1 | 24.0 | 23.9 |
| 12 | 123.8 | 123.8 | 123.8 | 123.8 | 123.7 | 123.8 | 123.7 | 124.0 |
| 13 | 142.8 | 142.8 | 142.8 | 142.8 | 142.8 | 142.8 | 142.8 | 142.9 |
| 14 | 41.8 | 41.7 | 41.7 | 41.7 | 41.7 | 41.7 | 41.6 | 41.7 |
| 15 | 34.9 | 34.9 | 34.9 | 34.8 | 34.9 | 34.8 | 34.8 | 34.9 |
| 16 | 68.5 | 68.5 | 68.7 | 68.5 | 68.5 | 68.7 | 68.7 | 68.5 |
| 17 | 48.3 | 48.3 | 48.0 | 48.3 | 48.3 | 48.1 | 48.0 | 48.4 |
| 18 | 40.1 | 40.0 | 40.1 | 40.0 | 40.0 | 40.1 | 40.1 | 40.1 |
| 19 | 47.3 | 47.3 | 47.3 | 47.2 | 47.2 | 47.2 | 47.2 | 47.3 |
| 20 | 36.5 | 36.4 | 36.4 | 36.3 | 36.3 | 36.4 | 36.4 | 36.5 |
| 21 | 79.3 | 79.2 | 79.3 | 78.7 | 78.8 | 78.8 | 78.8 | 79.2 |
| 22 | 74.0 | 74.0 | 73.6 | 73.9 | 74.0 | 73.6 | 73.6 | 74.0 |
| 23 | 22.7 | 22.5 | 22.5 | 22.7 | 22.5 | 22.5 | 22.5 | 28.1 |
| 24 | 62.9 | 63.3 | 63.3 | 62.8 | 63.3 | 62.9 | 63.3 | 16.9 |
| 25 | 15.5 | 15.6 | 15.6 | 15.5 | 15.6 | 15.5 | 15.6 | 15.7 |
| 26 | 16.8 | 16.7 | 16.7 | 16.7 | 16.7 | 16.7 | 16.7 | 14.7 |
| 27 | 27.6 | 27.5 | 27.6 | 27.6 | 27.5 | 27.6 | 27.6 | 27.6 |
| 28 | 63.4 | 63.4 | 63.6 | 63.4 | 63.5 | 63.6 | 63.6 | 63.4 |
| 29 | 29.6 | 29.6 | 29.6 | 29.5 | 29.5 | 29.6 | 29.6 | 29.6 |
| 30 | 20.2 | 20.2 | 20.2 | 20.2 | 20.3 | 20.3 | 20.2 | 20.2 |
| C21 | Tig | Tig | Tig | Ang | Ang | Ang | Ang | Tig |
| 1 | 168.1 | 168.1 | 167.9 | 167.9 | 167.9 | 167.7 | 167.7 | 168.1 |
| 2 | 129.5 | 129.5 | 129.5 | 129.2 | 129.2 | 129.0 | 129.0 | 129.5 |
| 3 | 136.7 | 136.7 | 136.9 | 136.6 | 136.7 | 137.2 | 137.1 | 136.7 |
| 4 | 14.2 | 14.2 | 14.2 | 15.8 | 15.8 | 15.9 | 15.8 | 14.2 |
| 5 | 12.4 | 12.4 | 12.5 | 21.0 | 21.0 | 21.1 | 21.1 | 12.4 |
| C22 | Tig | Tig | Ang | Tig | Tig | Ang | Ang | Tig |
| 1 | 168.5 | 168.5 | 168.3 | 168.3 | 168.4 | 168.2 | 168.2 | 168.5 |
| 2 | 129.2 | 129.2 | 129.2 | 129.2 | 129.2 | 129.0 | 129.0 | 129.2 |
| 3 | 137.0 | 137.0 | 136.6 | 137.2 | 137.2 | 137.1 | 137.3 | 137.0 |
| 4 | 14.1 | 14.1 | 15.8 | 14.1 | 14.1 | 15.8 | 15.9 | 14.1 |
| 5 | 12.3 | 12.3 | 20.9 | 12.3 | 12.3 | 20.9 | 20.9 | 12.3 |

TABLE 3

| | a Compound 4 | b Compound 1 | c Compound 2 | d Compound 5 | e Compound 3 | f — | g-1 — | g-2 Compound 6 |
|---|---|---|---|---|---|---|---|---|
| | $^{13}$C-NMR Data for the Sugar Moieties (125 MHz in Pyridine-d5) | | | | | | | |
| Glc-A | | | | | | | | |
| 1 | 104.9 | 104.7 | 104.7 | 104.9 | 104.7 | 104.8 | 104.6 | 105.1 |
| 2 | 78.8 | 79.7 | 79.7 | 78.7 | 79.7 | 78.8 | 79.8 | 82.4 |
| 3 | 76.4 | 76.5 | 76.5 | 76.4 | 76.4 | 76.4 | 76.5 | 75.9 |
| 4 | 82.5 | 81.9 | 81.9 | 82.5 | 81.8 | 82.6 | 82.0 | 81.9 |
| 5 | 75.7 | 75.8 | 75.7 | 75.7 | 75.7 | 75.7 | 75.8 | 75.7 |
| 6 | 172.2 | 172.1 | ND | ND | 172.0 | ND | ND | ND |
| Glc or Xyl or Gal | | | | | | | | |
| 1 | 104.9 | 104.3 | 104.3 | 104.8 | 104.3 | 104.8 | 104.3 | 106.7 |
| 2 | 75.7 | 75.8 | 75.8 | 75.7 | 75.8 | 75.7 | 75.7 | 74.6 |

TABLE 3-continued

13C-NMR Data for the Sugar Moieties (125 MHz in Pyridine-d5)

| | a<br>Compound 4 | b<br>Compound 1 | c<br>Compound 2 | d<br>Compound 5 | e<br>Compound 3 | f<br>— | g-1<br>— | g-2<br>Compound 6 |
|---|---|---|---|---|---|---|---|---|
| 3 | 78.5 | 78.1 | 78.1 | 78.5 | 78.1 | 78.5 | 78.1 | 74.9 |
| 4 | 70.8 | 69.7 | 69.8 | 70.8 | 69.8 | 70.8 | 69.8 | 69.5 |
| 5 | 67.2 | 78.4 | 78.4 | 67.2 | 78.4 | 67.2 | 78.4 | 76.9 |
| 6 | | 61.6 | 61.6 | | 61.6 | | 61.6 | 61.4 |
| Glc | | | | | | | | |
| 1 | 104.8 | 104.7 | 104.7 | 104.6 | 104.7 | 104.7 | 104.6 | 104.6 |
| 2 | 75.0 | 74.9 | 74.9 | 75.0 | 74.9 | 75.0 | 74.9 | 74.8 |
| 3 | 78.1 | 78.1 | 78.1 | 78.1 | 78.1 | 78.0 | 78.0 | 78.0 |
| 4 | 71.5 | 71.5 | 71.5 | 71.5 | 71.5 | 71.5 | 71.5 | 71.5 |
| 5 | 78.5 | 78.5 | 78.5 | 78.5 | 78.5 | 78.5 | 78.5 | 78.4 |
| 6 | 62.4 | 62.4 | 62.4 | 62.3 | 62.4 | 62.3 | 62.3 | 62.4 |

Glc-A: Glucuronic acid residue
ND: Not detected due to low signal intensity

Test Example 1

Measurement of Contraction Force Generated by Cells (1)

Measurement of contraction force generated by cells was carried out in a collagen gel culture system in accordance with the method of Kolodney et al. (Kolodney M S, Wysolmerski R B, Isometric contraction by fibroblasts and endothelial cells in tissue culture: a quantitative study. J Cell Biol., 117, 73-82 (1992); and Kolodney M S, Elson E L, Correlation of myosin light chain phosphorylation with isometric contraction of fibroblasts. J Biol Chem, 268, 23850-23855 (1993)).

Human skin fibroblasts (Dainippon Pharmaceutical Co., Ltd., Osaka, Japan, passage number: 3 to 8) were employed. A fibroblasts-embedded collagen gel ($1.5 \times 10^6$ cells, 1.5 mg/mL collagen, Nitta Gelatin Type I-A) was suspended and fixed in a beaker filled with about 70 mL of serum free medium (Dulbecco's modified Eagle's medium (DMEM)) which had been maintained at 37° C., and the collagen gel was stabilized for 1 hour under a tension of about 200 mg weight. Thereafter, a test substance diluted with a serum free DMEM to about 70 times of its final concentration in the fraction was added in an amount of 1.0 mL (final concentration: 3 μM). Contraction force generated by human skin fibroblasts was measured with an Isotonic Transducer (8 gf, T-7-8-240, ORIENTEC, JAPAN), and was recorded by a BIOPAC system (BIOPAC Systems, Inc., Santa Barbara, Calif., USA). The results are shown in Table 5.

Test Substance:

Among the saponins isolated in the Production Example described above, saponin b (compound 1), saponin c (compound 2), saponin e (compound 3) shown in Table 4 were used, and Escin Ia, Ib and saponin g-1 were used as controls for comparison.

TABLE 4

| | $R^1$ | $R^2$ | $R^4$ |
|---|---|---|---|
| Compound 1 | Tig | Tig | Glc |
| Compound 2 | Tig | Ang | Glc |

TABLE 4-continued

|  | R¹ | R² | R⁴ |
|---|---|---|---|
| Compound 3 | Ang | Tig | Glc |
| Escin Ia | Tig | Ac | Glc |
| Escin Ib | Ang | Ac | Glc |
| Saponin g-1 | Ang | Ang | Glc |

Ac =

Tig =

Ang = (structure shown)

TABLE 5

| Compound evaluated | Mean value of contraction force generated by cells (dyne) | SD value |
|---|---|---|
| Compound 1 | 7.4 | 3.99 |
| Compound 2 | 7.8 | 2.79 |
| Compound 3 | 7.7 | 2.26 |
| Escin Ia | 0.0 | — |
| Escin Ib | 0.0 | — |
| Saponin g-1 | 0.0 | — |

As shown in Table 5, Escin Ia, Ib and saponin g-1 showed no enhancement in the contraction force generated by fibroblasts, but the compound of the present invention showed a significant enhancement in the contraction force generated by fibroblasts.

Test Example 2

Measurement of Contraction Force Generated by Cells (2)

Among the saponins isolated in the Production Example described above, the contraction force generated by fibroblasts added saponin b (compound 1) or saponin a (compound 4) shown in Table 6, was measured by the same method as in Test Example 1. The results are shown in Table 7.

TABLE 6

|  | $R^1$ | $R^2$ | $R^4$ |
|---|---|---|---|
| Compound 1 | Tig | Tig | Glc |
| Compound 4 | Tig | Tig | Xyl |

TABLE 7

| Compound evaluated | Mean value of contraction force generated by cells (dyne) | SD value |
|---|---|---|
| Compound 1 | 17.0 | 3.0 |
| Compound 4 | 25.0 | 10.0 |

As shown in Table 7, it was confirmed that compound 4 which had a different type of binding sugar moiety also enhanced the contraction force generated by fibroblasts.

Production Example 2

Preparation of Sample Evaluated By Human

To 100 g of a ground product of horse chestnut seeds having the hulls removed, 1 L of 75 volt ethanol was added, and the mixture was extracted while being stirred for 6 hours under heating at 50° C. The extract was cooled to room temperature, and then filtered. 1 L of 75 vol % ethanol was added to the residue to conduct extraction again under the same conditions, and the extract was filtered. The two filtrates were combined, 240 g of 1,3-butylene glycol was added thereto, and the resulting mixture was concentrated under reduced pressure. The concentrate was left to stand still for one week at a low temperature, and then filtered to remove any insoluble components. 1,3-Butylene glycol and water were added to the resultant product to prepare 3.5 L of 80% 1,3-butylene glycol solution (solid content: 0.5% by mass) which included the compound of the present invention at a high concentration. This was used as a solution of the terpenoid saponins mixture of the present invention. The present solution of terpenoid saponins mixture contained 0.02% by mass in total of the compounds 1 to 6.

Test Example 3

Test on Humans (1) Test Design

Double-blind comparative test was carried out on a half-face of seven healthy female subjects (age: 30s to 40s) having wrinkles at the outer corners of their eyes to compare a test sample containing the solution of terpenoid saponins mixture prepared in Production Example 2 and a placebo sample not containing only the solution of terpenoid compound mixture. Each subject was applied a predetermined sample to the area around her eye every day, two times or three times a day, for 2 months.

Table 8 shows the formulations of samples tested.

TABLE 8

| Ingredients (% by mass) | Test sample | Placebo |
|---|---|---|
| Inventive solution of terpenoid saponins mixture | 3.0 | — |
| Xanthan gum | 0.1 | 0.1 |
| 86% Glycerin | 5.0 | 5.0 |
| Methylpolysiloxane | 4.0 | 4.0 |
| Carboxyvinyl polymer | 0.4 | 0.4 |
| Potassium hydroxide | 0.6 | 0.6 |
| Cetyl dimethylbutyl ether | 0.1 | 0.1 |
| Neopentyl glycol dicaprate | 0.1 | 0.1 |
| 1,3-Butylene glycol | 3.0 | 3.0 |
| Polyethylene glycol | 3.0 | 3.0 |
| Succinic acid | 0.3 | 0.3 |
| Polyoxyethylene hydrogenated castor oil | 0.5 | 0.5 |
| Antiseptic | 0.3 | 0.3 |
| Fragrance | Trace amount | Trace amount |
| 95% Synthetic alcohol | 0.5 | 0.5 |
| Purified water | Balance | Balance |

(2) Method of Evaluating Efficacy of Samples on Wrinkles (A) Scores Determined Through Visual Observation of Photographs Areas around the right and left eyes of each subject who was sitting and lightly closing the eyes were photographed with a digital camera (close-up photography) and then printed on 2 L-size sheets.

The samples were evaluated on the basis of the degree of wrinkles at the outer corners of the eyes observed in the photographs according to the following ratings: score 0: no wrinkle, score 1: a few wrinkles, score 2: some wrinkles, score 3: many wrinkles, and score 4: considerable wrinkles (in increments of 0.25 from score 1 to 5; i.e., a total of 17 levels). The score at the time of initiation of the two-month test was subtracted from the score at the time of termination of the test (test period: 2 months), and the samples were compared in terms of change in score.

(B) Analysis of Roughness on Replica

Figure 1:
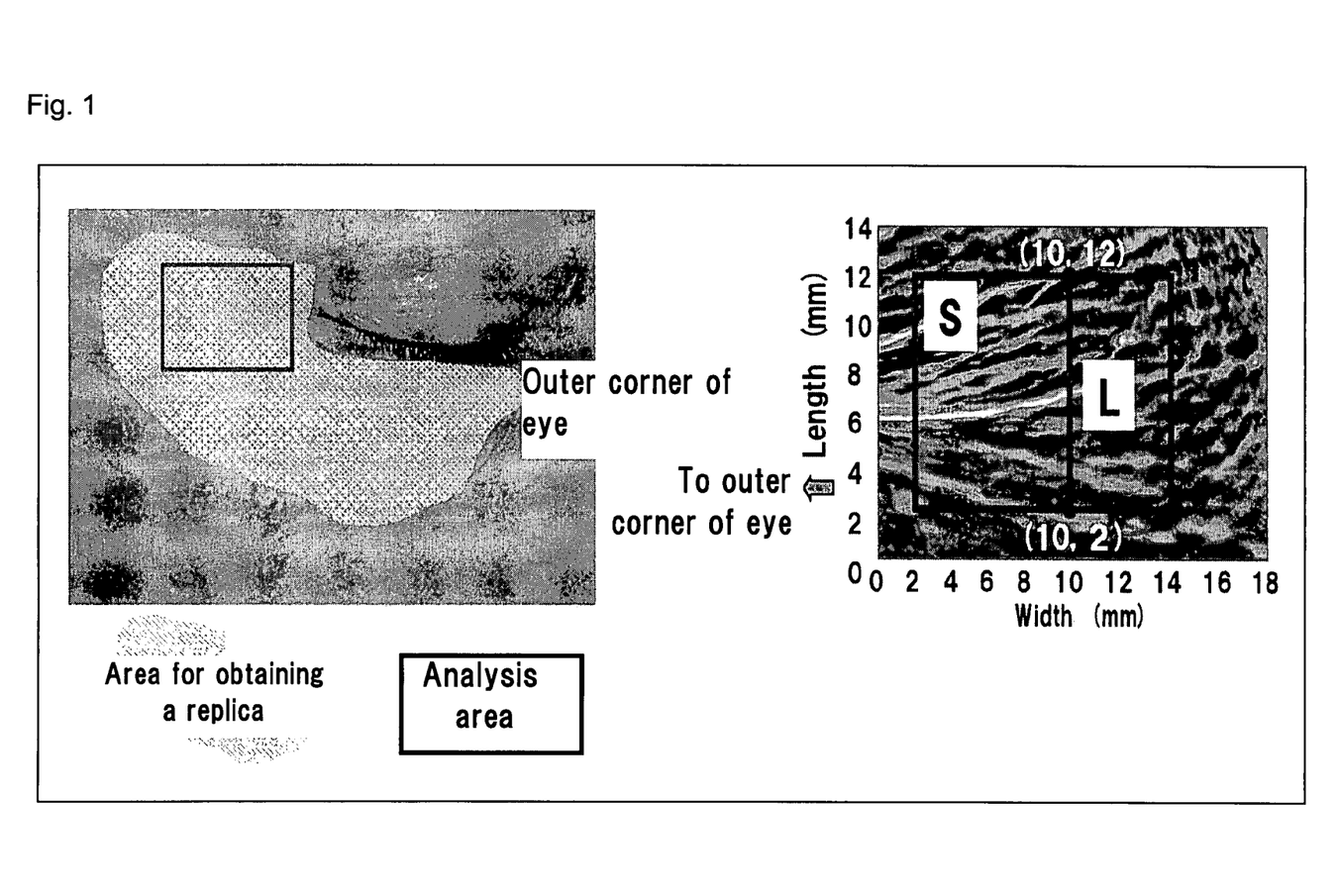
FIG. 1 shows the facial area from which a replica was obtained for line roughness analysis, and an analysis area of the replica (L: line located 10 mm away from the end on the side of the outer corner of the eye (L=10 mm), S: region of 2 mm to 14 mm away from the end on the side of the outer corner of the eye (area=12 mm×10 mm)).

Replicas (GC Exafine, GC Co., Ltd., Tokyo, Japan) of facial areas around the right and left eyes were taken from each subject who was lying on her back and lightly closing the eyes. The thus-prepared replicas were subjected to three-dimensional roughness analysis (PRIMOS compact, GF Messetechnik GmbH, Berlin). FIG. 1 shows the facial area from which a replica was obtained, and an area employed for analysis.

By use of PRIMOS software (English version 4.0), configuration matching was carried out between a replica obtained at the time of initiation of the two-month test (reference) and a corresponding replica obtained at the time of termination of the test. As shown in FIG. 1, the site at which the configurations of the replicas were matched was designated as an area for roughness analysis of the outer corner of the eye. Line roughness and surface roughness in the area were determined by use of the software. The line roughness parameters employed were Ra (arithmetical mean roughness) and Rz (10-point mean roughness), and the surface roughness parameters employed were Sa (arithmetical mean height) and Sz (maximum height of scale limited surface).

(3) Results

Figure 2:
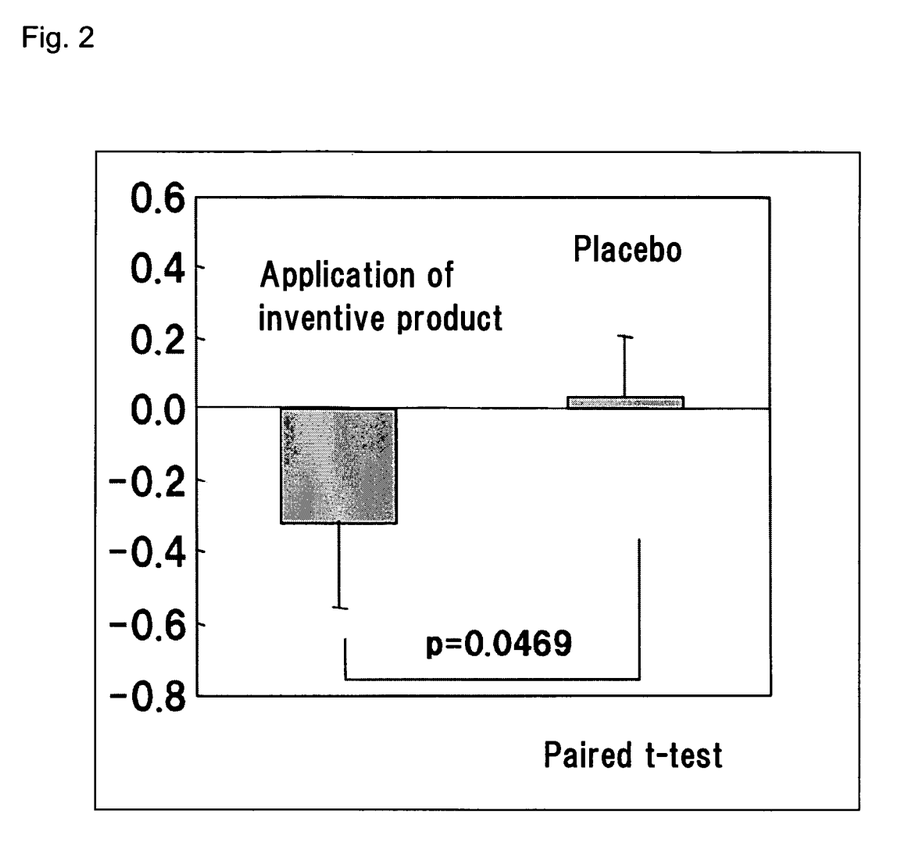
FIG. 2 shows change in the scores determined through visual observation of photographs of the outer corners of the eyes.

1) FIG. 2 shows change in the scores determined through visual observation of photographs of the outer corners of the eyes.

In the placebo group, no significant difference was observed between the score at the time of initiation of the two-month test and that at the time of termination of the test. In contrast, in the group applied the solution of terpenoid saponins mixture of the present invention, a significant reduction in score was observed.

Figure 3:
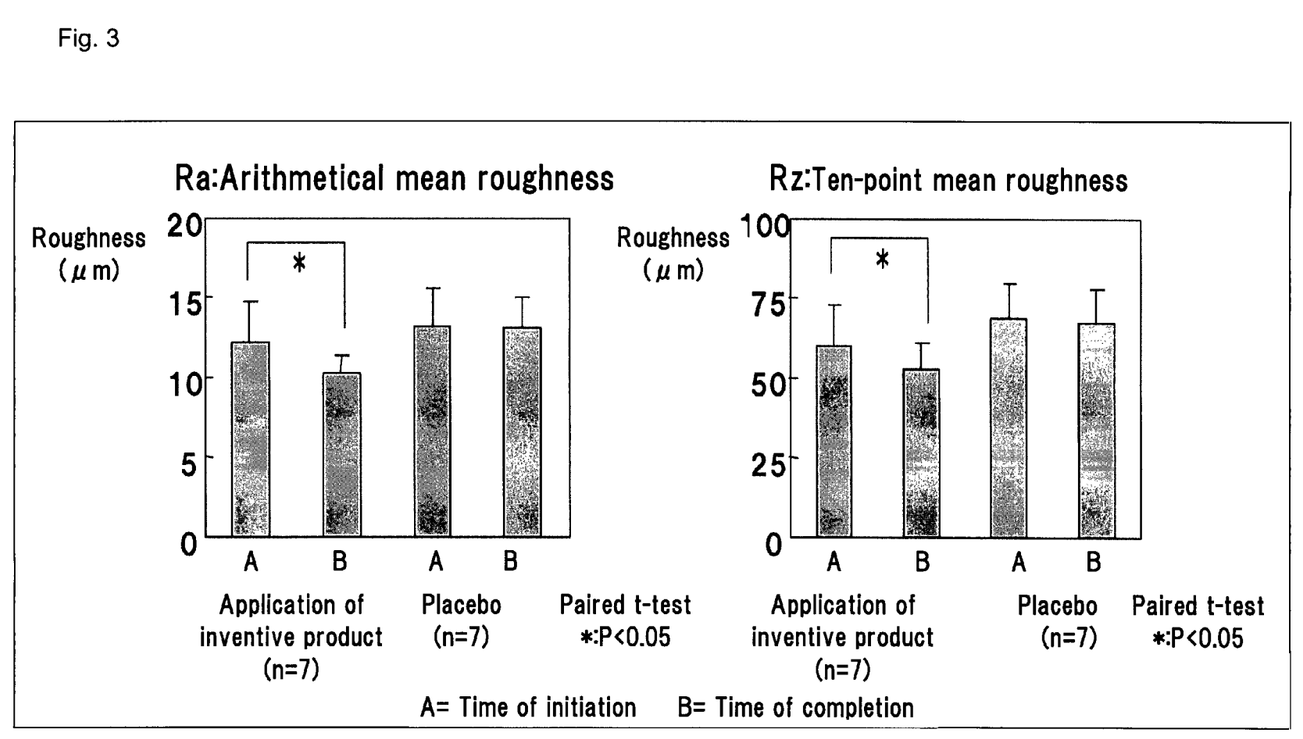
FIG. 3 shows data of Ra and Rz obtained through line roughness analysis of replicas.
Figure 4:
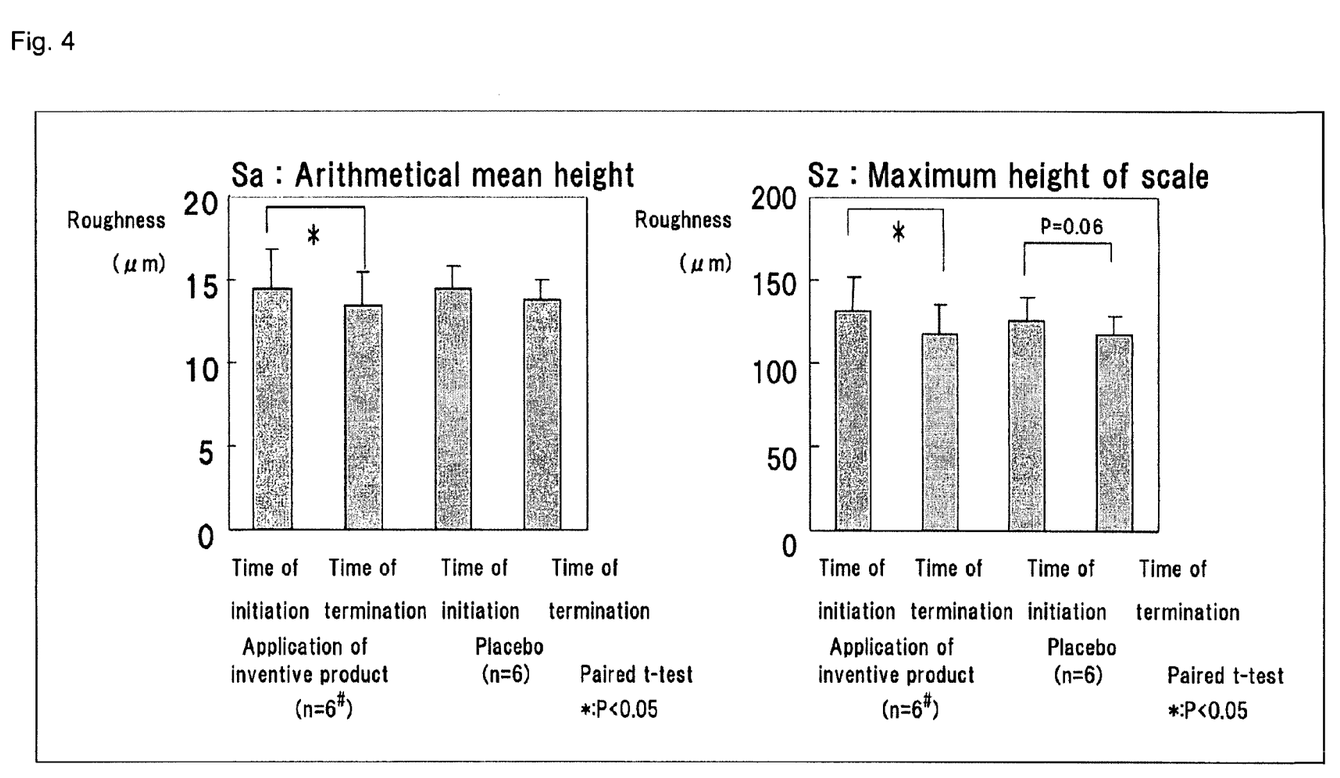
FIG. 4 shows data of Sa and Sz obtained through surface roughness analysis of replicas (#: analysis data of replicas from six subjects (n=6), exclusive of one in which air bubbles were included.

2) FIG. 3 shows data of Ra and Rz obtained through line roughness analysis of replicas. FIG. 4 shows data of Sa and Sz obtained through surface roughness analysis of replicas (FIG. 4 shows analysis data of six subjects exclusive of one subject, as the replica from the one subject has air bubbles in the area for analysis.

In the placebo group, line roughness analysis showed no significant difference between data at the time of initiation of the test and those at the time of termination of the test. In contrast, in the group applied the solution of terpenoid saponins mixture of the present invention, a significant difference was observed between line roughness at the time of initiation of the test and that at the time of termination of the test; i.e., a significant reduction in Ra and Rz was observed.

Similar to the above case, surface roughness analysis in the placebo group showed no significant difference between data at the time of initiation of the test and those at the time of termination of the test. In contrast, in the group applied the solution of terpenoid saponins mixture of the present invention, a significant reduction in Sa and Sz was observed.

The invention claimed is:

1. A method for ameliorating skin aging, comprising applying, to a human body, a preparation that comprises 0.00001 to 2% by mass of one or more purified triterpenoid saponins represented by formula (1):

wherein at least one of $R^1$ and $R^2$ is a tigloyl group, and the other is a tigloyl group or an angeloyl group; $R^3$ is a methyl group or a hydroxymethyl group; and $R^4$ is glucose, xylose or galactose; and wherein said preparation does not contain escin Ia or escin Ib.

2. The method of claim 1, wherein said preparation comprises one said triterpenoid saponin represented by said formula (1).

3. The method of claim 1, wherein said preparation comprises more than one of said triterpenoid saponins of formula (1).

4. The method of claim 1, wherein said preparation comprises a triterpenoid saponin of formula (1) in which $R^1$ is a tigloyl group, $R^2$ is a tigloyl group, $R^3$ is a hydroxymethyl group and $R^4$ is glucose.

5. The method of claim 1, wherein said preparation comprises a triterpenoid saponin of formula (1) in which $R^1$ is a tigloyl group, $R^2$ is an angeloyl group, $R^3$ is a hydroxymethyl group and $R^4$ is glucose.

6. The method of claim 1, wherein said preparation comprises a triterpenoid saponin of formula (1) in which $R^1$ is an angeloyl group, $R^2$ is a tigloyl group, $R^3$ is a hydroxymethyl group and $R^4$ is glucose.

7. The method of claim 1, wherein said preparation comprises a triterpenoid saponin of formula (1) in which $R^1$ is a tigloyl group, $R^2$ is a tigloyl group, $R^3$ is a hydroxymethyl group and $R^4$ is xylose.

8. The method of claim 1, wherein said preparation comprises a triterpenoid saponin of formula (1) in which $R^1$ is an angeloyl group, $R^2$ is a tigloyl group, $R^3$ is a hydroxymethyl group and $R^4$ is xylose.

9. The method of claim 1, wherein said preparation comprises a triterpenoid saponin of formula (1) in which $R^1$ is a tigloyl group, $R^2$ is a tigloyl group, $R^3$ is a methyl group and $R^4$ is galactose.

10. The method of claim 1, wherein the amount of said triterpenoid saponins represented by formula (1) in said preparation is 0.0001 to 0.5% by mass.

11. The method of claim 10, wherein the amount of said triterpenoid saponins represented by formula (1) in said preparation is 0.001 to 0.1% by mass.

* * * * *